(12) United States Patent
Chan

(10) Patent No.: US 7,806,592 B1  
(45) Date of Patent: Oct. 5, 2010

(54) LASER ANGLE GUIDE ASSEMBLY FOR COMPUTED TOMOGRAPHY AND METHOD FOR OPERATING THE SAME

(76) Inventor: Wing-Sheung Chan, 5F, No. 10, Lane 47, Yuying St., Taiping City, Taichung Hsien (TW)

( * ) Notice: Subject to any disclaimer, the term of this patent is extended or adjusted under 35 U.S.C. 154(b) by 0 days.

(21) Appl. No.: 12/485,280

(22) Filed: Jun. 16, 2009

(51) Int. Cl.  
*A61B 6/08* (2006.01)

(52) U.S. Cl. .................................. 378/206; 606/130

(58) Field of Classification Search ............... 378/204, 378/205, 206, 210; 606/130  
See application file for complete search history.

(56) References Cited

U.S. PATENT DOCUMENTS

| | | | | |
|---|---|---|---|---|
| 5,517,546 A | * | 5/1996 | Schmidt | 378/206 |
| 5,598,269 A | * | 1/1997 | Kitaevich et al. | 378/206 |
| 5,782,842 A | * | 7/1998 | Kloess et al. | 378/206 |
| 6,006,126 A | * | 12/1999 | Cosman | 606/130 |
| 6,044,291 A | * | 3/2000 | Rockseisen | 378/206 |
| 6,810,595 B2 | * | 11/2004 | Chan | 606/130 |

* cited by examiner

*Primary Examiner*—Chih-Cheng G Kao  
(74) *Attorney, Agent, or Firm*—Rabin & Berdo, P.C.

(57) ABSTRACT

A laser angle guide assembly has a stand, a laser guide and a reflector. The laser guide is mounted adjustably on the stand and has a body, a side index line, a front index line and an index protrusion. The side index line is formed on the side faces of the body. The front index line is formed on the front face of the body. The index protrusion is formed on the front surface at the bottom of the body and has an inclined top and a front face. The reflector is attached and inclined relative to the front surface of the laser guide at an angle and has a reflecting side facing to the inclined top of the index protrusion. Accordingly, the laser angle guide assembly can provide a guide effect to help a doctor to puncture a needle assembly at a desired angle precisely.

13 Claims, 7 Drawing Sheets

ADJUSTING A BODY OF A LASER GUIDE TO AN ANGLE

MOVING THE LASER ANGLE GUIDE ASSEMBLY TO A LOCATION BETWEEN TWO STATIONARY LASER GENERATORS

ADJUSTING POSITION AND ANGLE OF THE LASER ANGLE GUIDE ASSEMBLY

EMITTING A FRONT LASER FROM AN ADJUSTABLE LASER GENERATOR ONTO A FRONT SURFACE OF THE LASER GUIDE

ADJUSTING POSITION AND ANGLE OF ADJUSTABLE LASER GENERATOR TO MAKE A REFLECTED LASER LINE OVERLAPPING WITH THE FRONT LASER TO A SINGLE LINE

FIG.7

LASER ANGLE GUIDE ASSEMBLY FOR COMPUTED TOMOGRAPHY AND METHOD FOR OPERATING THE SAME

BACKGROUND OF THE INVENTION

1. Field of the Invention

The present invention relates to a laser angle guide assembly, and more particularly to a laser angle guide assembly for computed tomography (CT) and a method for the same.

2. Description of Related Art

Computed tomography is a way to scan a patient for biopsy, and a specimen of tissue will be removed from the patient and be examined by a pathologist to check diseases, such as cancer. A doctor will remove a specimen of tissue from the patient with puncturing a needle assembly in to a patient's body at a desired position, angle and depth determined by the computed tomography. However, there is no guide for the puncturing angle during the specimen process, so a laser angle guide assembly is provided to generate an index line to help a doctor to puncture the needle assembly into the patient's body.

However, during the puncturing process, the laser angle guide assembly has to be removed so that the angle for the needle assembly puncturing into the patient's body also has to be dependent on the experience and the intuition of the doctor. If the puncturing angle has a large deviation relative to the desired puncturing angle, this will cause pain to the patient and even to lead complications to the patient.

To overcome the shortcomings, the present invention tends to provide a laser angle guide assembly to mitigate or obviate the aforementioned problems.

SUMMARY OF THE INVENTION

The main objective of the invention is to provide a laser angle guide assembly that can provide a guide effect to help a doctor to puncture a needle assembly at a desired angle precisely. The laser angle guide assembly has a stand, a laser guide and a reflector. The laser guide is mounted adjustably on the stand and has a body, a side index line, a front index line and an index protrusion. The body has a front face, two side faces, a top and a bottom. The side index line is formed on the side faces of the body. The front index line is formed on the front face of the body. The index protrusion is formed on the front surface at the bottom of the body and has an inclined top and a front face. The reflector is attached and inclined relative to the front surface of the laser guide at an angle and has a reflecting side facing to the inclined top of the index protrusion.

Other objects, advantages and novel features of the invention will become more apparent from the following detailed description when taken in conjunction with the accompanying drawings.

BRIEF DESCRIPTION OF THE DRAWINGS

FIG. 7 is a block diagram of a method of operating the laser angle guide assembly in accordance with the present invention.

DETAILED DESCRIPTION OF PREFERRED EMBODIMENT

Figure 1:
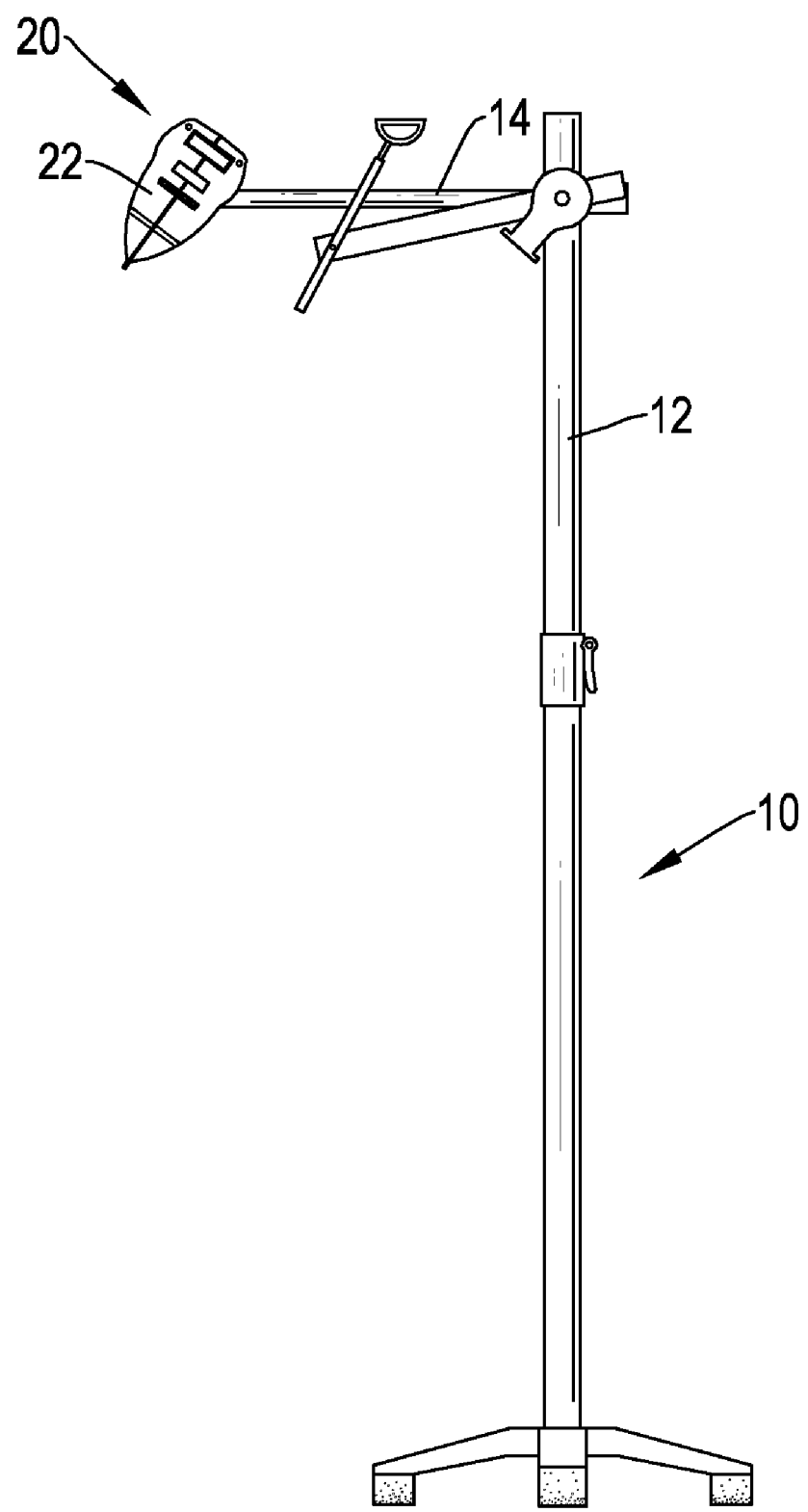
FIG. 1 is a perspective view of a laser angle guide assembly in accordance with the present invention.
Figure 2:
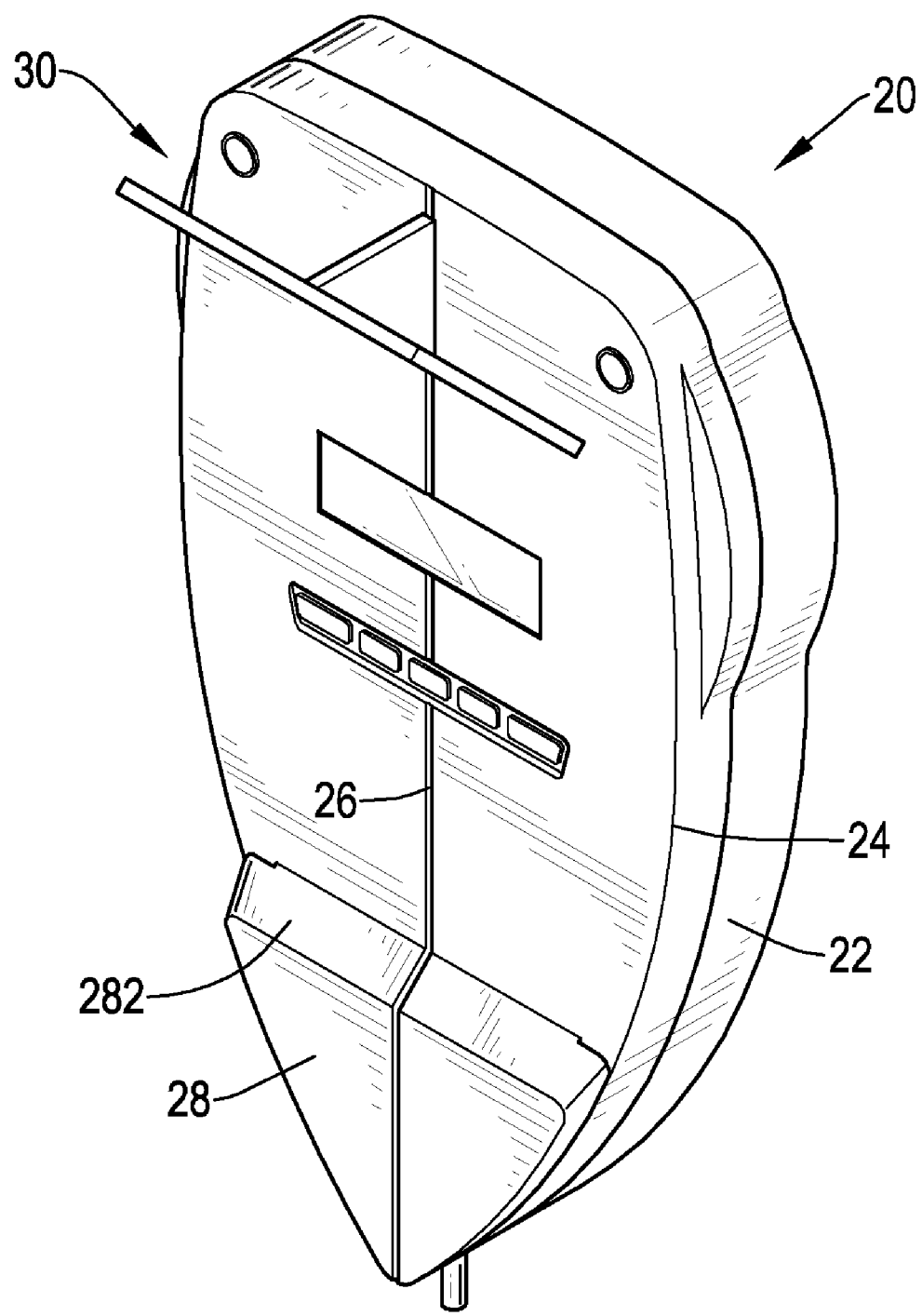
FIG. 2 is an enlarged perspective view of the laser guide of the laser angle guide assembly in FIG. 1.
Figure 3:
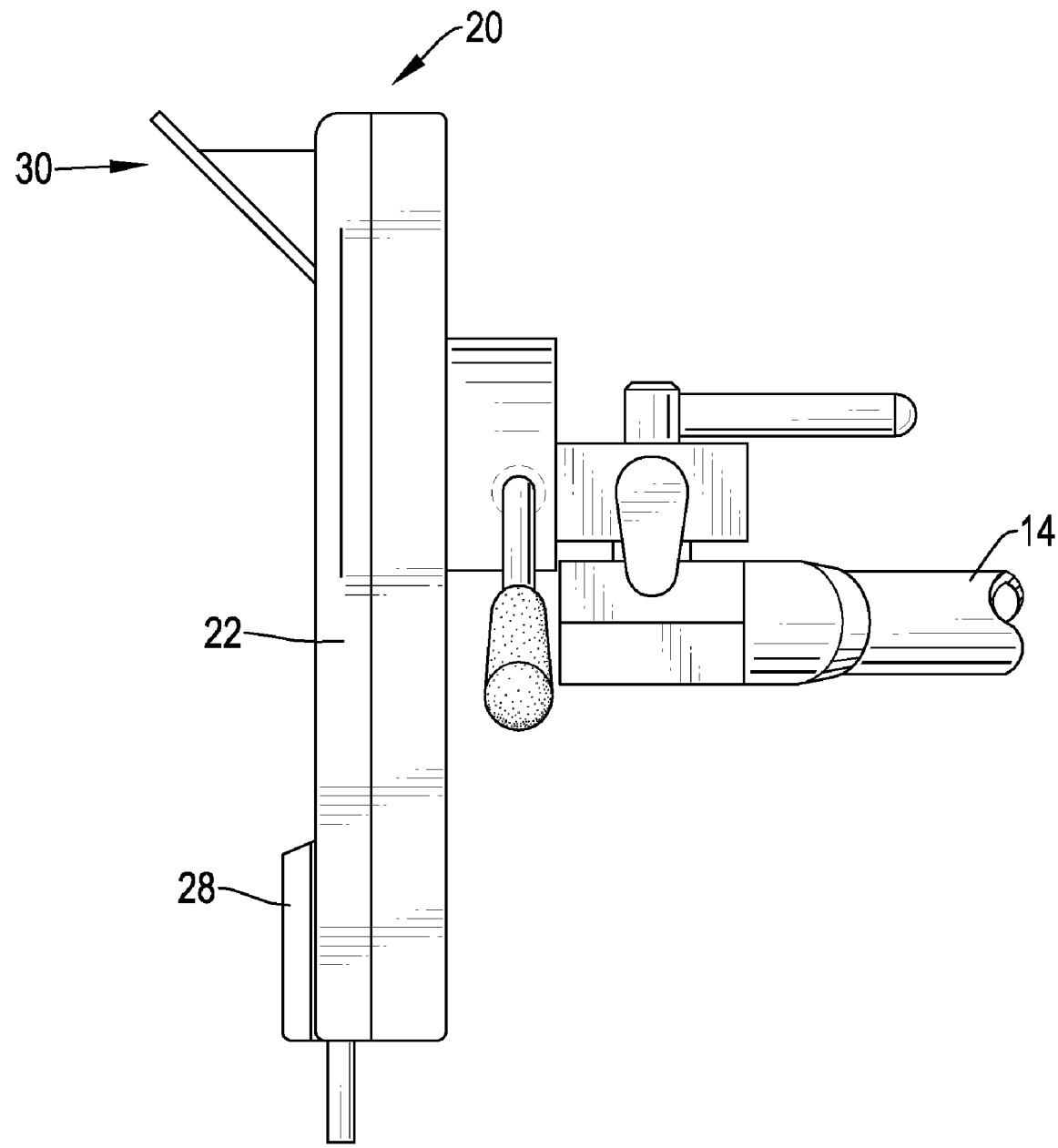
FIG. 3 is a side view of the laser guide of the laser angle guide assembly in FIG. 1.

With reference to FIGS. 1 to 3, a laser angle guide assembly for a puncturing process with computed tomography (CT) in accordance with the present invention comprises a stand (10), a laser guide (20) and a reflector (30). The stand (10) comprises a base, a post (12) and a lateral rod (14). The post (12) is mounted on and protrudes upward from the base. The lateral rod (13) is laterally mounted near the top end of the post (12).

The laser guide (20) is mounted adjustably on the lateral rod (14) at angle. In practice, the laser guide (20) may be connected to the lateral rod (14) with a universal joint or at least one pivot pin that is rotatably mounted between the laser guide (20) and the lateral rod (14) to make the angle of the laser guide (20) adjustable relative to the lateral rod (14). The laser guide (20) has a body (22) having a front face, two side faces, two side edges, a top, a bottom, a side index line (24), a front index line (26) and an index protrusion (28). The side edges are defined respectively between the front face and the side faces. The side index line (24) and the front index line (26) are defined in the body (22) respectively at two perpendicular surfaces of the body (22). In practice, the side index line (24) may be a single line mounted over the side faces and the top of the body (22) or be implemented as two line segments mounted respectively on the side surfaces and aligning with each other. In a preferred embodiment, the side edges may serve as the line segments of the side index line (24). The front index line (26) is defined in the front surface of the body (22). The index lines (24,26) may be implemented as ribs or grooves or be printed on the body (22). The index protrusion (28) is formed on the front surface at the bottom of the body (22). The index protrusion (28) has an inclined top (282) and a front face. The front index line (26) is formed on the front surface from the top to the bottom of the body (22) through the inclined top (282) and the front face of the index protrusion (28).

The reflector (30) may be a mirror and is attached and inclined relative to the front surface of the body (22) the laser guide (20) at a specific angle. The reflector (30) has a reflecting side facing to the inclined top (282) of the index protrusion (28).

In use, with further reference to FIGS. 4 to 7, the body (22) of the laser guide (20) is adjusted to a specific angle relative to the lateral rod (14) of the stand (10) according to an angle determined by the computed tomography. The laser angle guide assembly is moved into a surgery room between two stationary laser generators (60) and above a patient lies on a bed. The position and angle of the stand (10) is moved to a position where two side lasers emitting from the stationary laser generators (60) overlap respectively the side index line (24) on the laser guide (20). When the side edges of the body (22) of the laser guide (20) serves as the side index line (24), a laser line will be formed on the inclined top (282) of the index protrusion (28) to improve the identification of the alignment between the side index line (24) with the side lasers.

Figure 4:
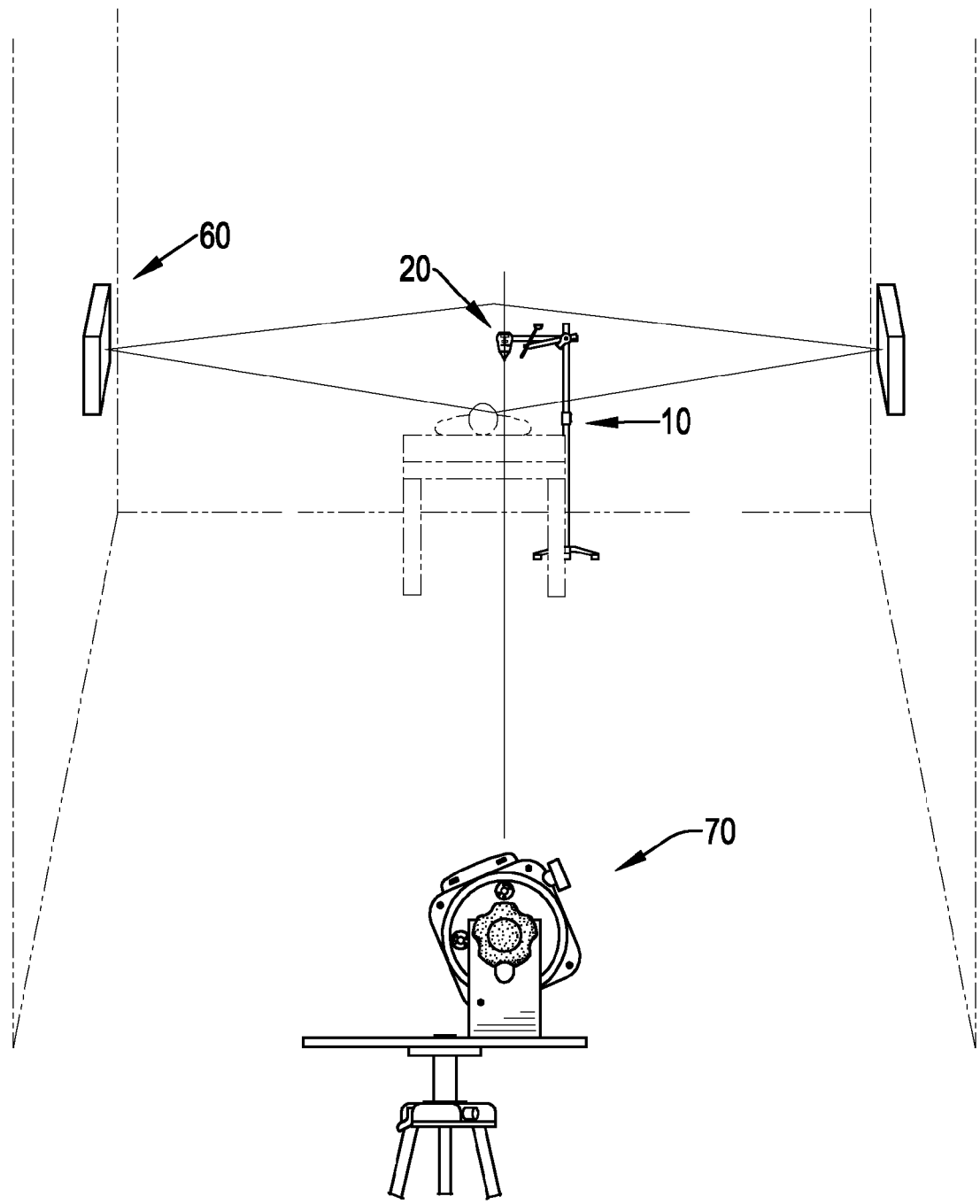
FIG. 4 is an operational perspective view of the laser angle guide assembly in FIG. 1.
Figure 5:
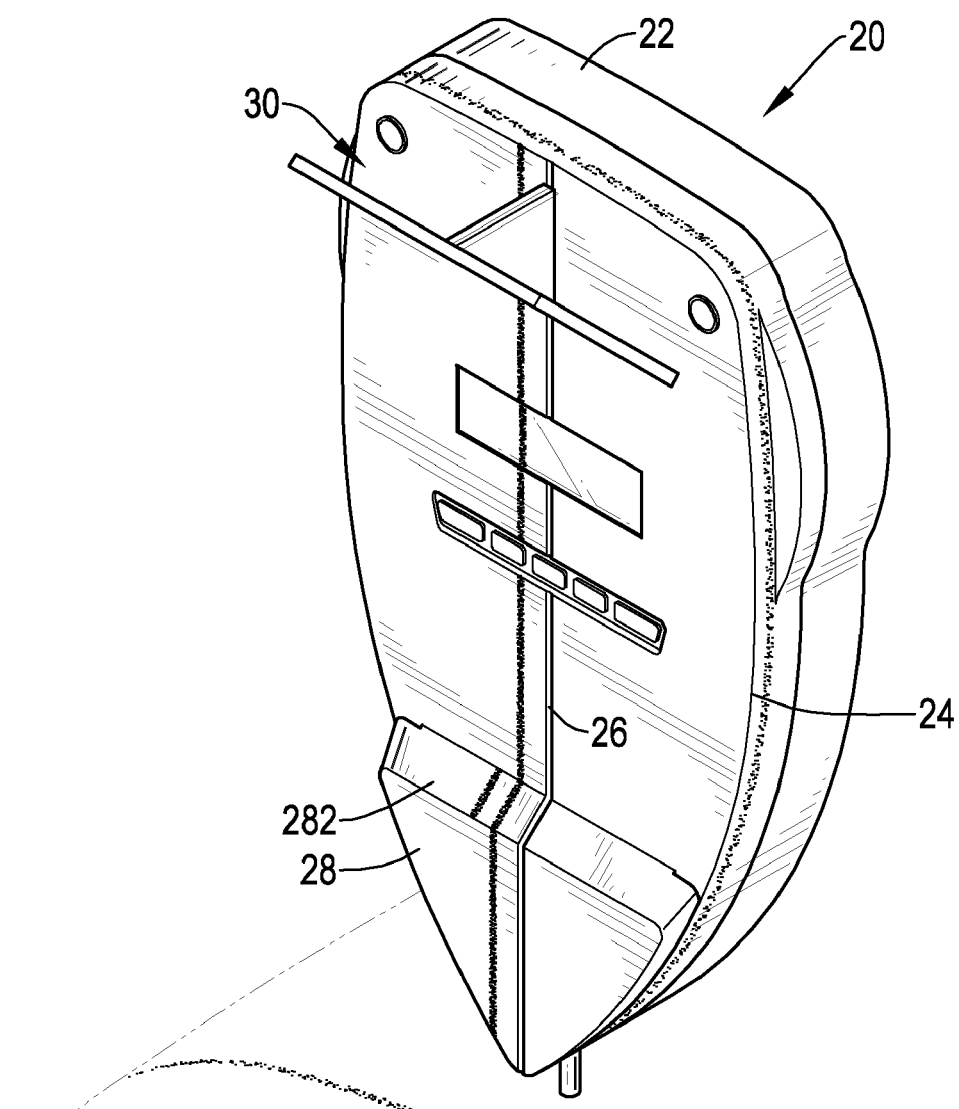
FIG. 5 is an operational perspective view of the laser guide of the laser angle guide assembly in FIG. 2 for adjusting the position of the laser guide according to two side lasers and an angle of a front laser emitting from an adjustable laser generator according to the angle of the laser guide.
Figure 6:
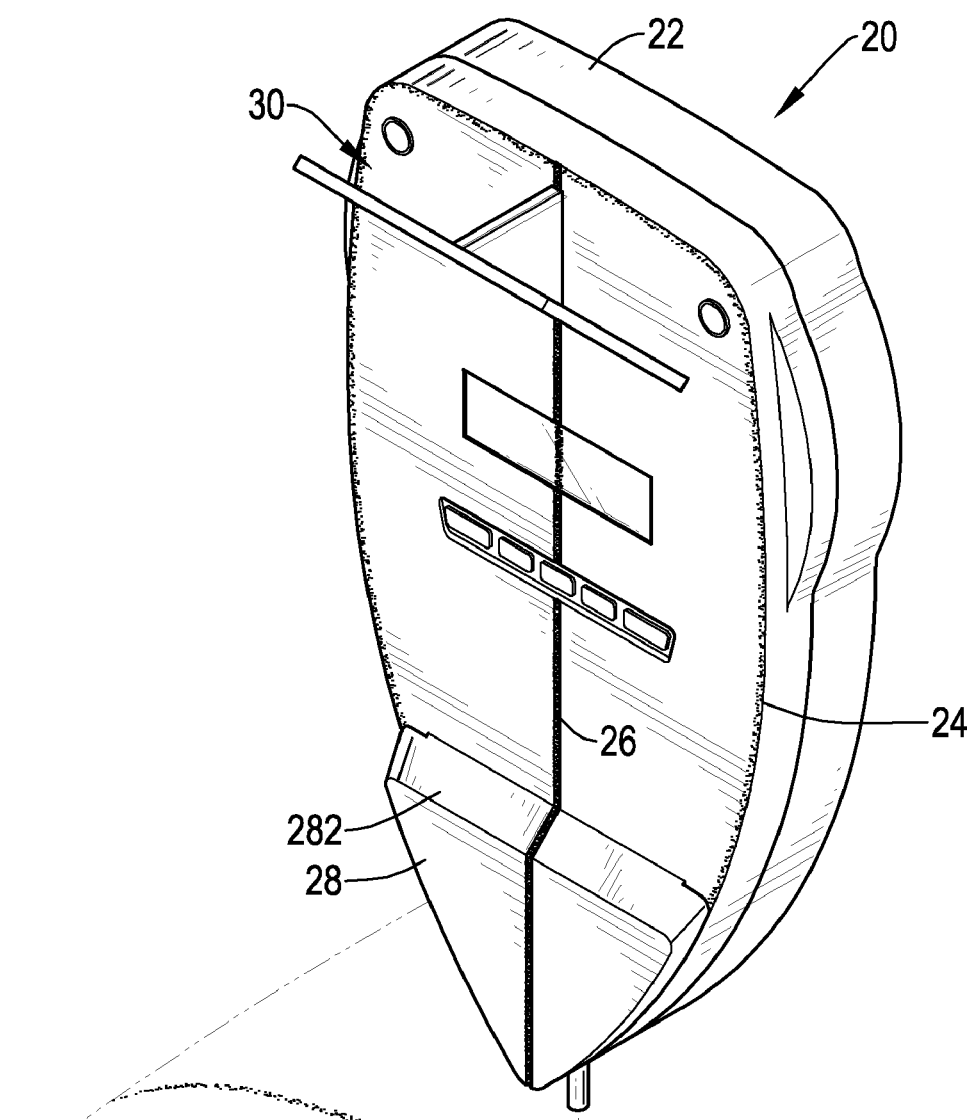
FIG. 6 is an operational perspective view of the laser guide of the laser angle guide assembly in FIG. 2 showing that the angle and the position of the front laser has been adjusted.

An adjustable laser generator (70) is arranged in front of the laser angle guide assembly and emits a front laser onto the front surface of the body (22) of the laser guide (20). The adjustable laser generator (70) is moved to a position where the front laser overlaps the front index line (26) on the front surface of the body (22) of the laser guide (20). When the front laser projects onto the front face of the body (22), a reflected laser line will occur by the reflector (30) and projects onto the front surface of the body (22) and the index protrusion (28). If the angle of the front laser projecting onto the laser guide (20) is not at the angle of the body (22) of the laser guide (20), the reflected laser line is separate from the front laser projecting onto the front surface of the body (22) as shown in FIG. 4. At this time, the angle of the adjustable laser generator (70) is adjusted to make the reflected laser line and the front laser overlapping with each other to form a single line on the front face of the body (22). Accordingly, the front laser is at angle same as that determined by the computed tomography. With the inclined top (282) of the index protrusion (28), the reflected laser line from the reflector (30) will project on the inclined top (282) to provide a clear auxiliary identification effect.

Accordingly, after the laser angle guide assembly is removed, the front laser can provide a guide effect to a doctor to puncture a needle assembly into a patient's body at an angle precisely based on the results of the computed tomography and to keep the patient from pain and complications. In addition, the side lasers and the front laser can be in different colors to improve the identification of the lasers. For example, the side lasers can be in red, and the front laser can be in green.

Even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A laser angle guide assembly comprising:
   a stand;
   a laser guide mounted adjustably on the stand and having
      a body having a front face, two side faces, a top and a bottom;
      a side index line formed on the side faces of the body;
      a front index line formed on the front face of the body; and
      an index protrusion formed on the front surface at the bottom of the body and having an inclined top and a front face; and
   a reflector attached and inclined relative to the front surface of the laser guide at an angle and having a reflecting side facing to the inclined top of the index protrusion.

2. The laser angle guide assembly as claimed in claim 1, wherein
   the stand comprises
      a base;
      a post mounted on and protruding upward from the base and having a top end; and
      a lateral rod laterally mounted near the top end of the post; and
   the laser guide is mounted on the lateral rod.

3. The laser angle guide assembly as claimed in claim 2, wherein the side index line is implemented as two line segments aligning with each other and mounted respectively on the side surfaces.

4. The laser angle guide assembly as claimed in claim 3, wherein the line segments of the side index line are mounted respectively on two side edges defined respectively between the front face and the side faces of the body of the laser guide.

5. The laser angle guide assembly as claimed in claim 4, wherein the reflector is a mirror.

6. The laser angle guide assembly as claimed in claim 5, wherein the front index line is formed on the front surface from the top to the bottom of the body through the inclined top and the front face of the index protrusion.

7. The laser angle guide assembly as claimed in claim 1, wherein the side index line is implemented as two line segments aligning with each other and mounted respectively on the side surfaces.

8. The laser angle guide assembly as claimed in claim 7, wherein the line segments of the side index line are mounted respectively on two side edges defined respectively between the front face and the side faces of the body of the laser guide.

9. The laser angle guide assembly as claimed in claim 1, wherein the reflector is a mirror.

10. The laser angle guide assembly as claimed in claim 1, wherein the front index line is formed on the front surface from the top to the bottom of the body through the inclined top and the front face of the index protrusion.

11. A method of operating a laser angle guide assembly as claimed in claim 1 comprising acts of:
   adjusting a body of a laser guide to a specific angle relative to a stand according to an angle determined by a computed tomography;
   moving the laser angle guide assembly to a location between two stationary laser generators;
   adjusting a position and an angle of the stand to a position where two side lasers emitting from the stationary laser generators overlap with a side index line defined on the laser guide;
   emitting a front laser from an adjustable laser generator onto a front surface of the body of the laser guide;
   adjusting a position and an angle of the adjustable laser generator to a position where the front laser overlaps with a front index line on the body of the laser guide and a reflected laser line reflected from a reflector on the body overlaps the front laser to form a single line.

12. The method of operating a laser angle guide assembly as claimed in claim 11, wherein the side lasers and the front laser are in different colors.

13. The method of operating a laser angle guide assembly as claimed in claim 12, wherein the side lasers are in red and the front laser is in green.

* * * * *